(12) United States Patent
Garcia Lara et al.

(10) Patent No.: US 8,691,242 B2
(45) Date of Patent: Apr. 8, 2014

(54) STAPHYLOCOCCUS AUREUS DIV1B FOR USE AS VACCINE

(75) Inventors: Jorge Garcia Lara, Sheffield (GB); Simon Foster, Hathersage (GB)

(73) Assignee: Absynth Biologics Limited, Sheffeield (GB)

( * ) Notice: Subject to any disclaimer, the term of this patent is extended or adjusted under 35 U.S.C. 154(b) by 0 days.

(21) Appl. No.: 13/500,292

(22) PCT Filed: Sep. 13, 2010

(86) PCT No.: PCT/GB2010/001722
§ 371 (c)(1),
(2), (4) Date: Apr. 4, 2012

(87) PCT Pub. No.: WO2011/042681
PCT Pub. Date: Apr. 14, 2011

(65) Prior Publication Data
US 2012/0195920 A1 Aug. 2, 2012

(30) Foreign Application Priority Data
Oct. 9, 2009 (GB) .................................. 0917685.0

(51) Int. Cl.
*A61K 39/085* (2006.01)
*A61K 39/02* (2006.01)
*C12P 21/04* (2006.01)
*C07H 21/04* (2006.01)

(52) U.S. Cl.
USPC .................. 424/243.1; 424/184.1; 424/190.1; 514/2; 530/350; 536/23.5; 536/23.7

(58) Field of Classification Search
None
See application file for complete search history.

(56) References Cited

FOREIGN PATENT DOCUMENTS

| EP | 0 854 186 A2 | 7/1998 |
| WO | WO02077183 | * 10/2002 |
| WO | 02/094868 A2 | 11/2002 |

OTHER PUBLICATIONS

Ellis, R.W. "Vaccines" .Plotkin, S.A. et al. (eds) published by W. B. Saunders company (Philadelphia). Chapter 29, 1988.*
Abbas et al. Cellular and Molecular Immunology 2000 Chapter 15 p. 360-362.*
Harlow et al. Antibodies A Laboratory Manual, 1988 Chapter 5, p. 72-74.*
Absynth Biologics Limited, "International Search Report and Written Opinion," Int'l Patent Application No. PCT/GB2010/001722, filed Sep. 13, 2010 (Jan. 28, 2011).
Garcia-Lara, Jorge et al., "Anti_*Staphylococcus aureus* immunotherapy: current status and prospects," Current Opinion in Pharmacology, vol. 9, No. 5, pp. 552-557 (Sep. 3, 2009).
Garcia-Lara, Jorge et al., "*Staphylococcus aureus*: the search for novel targets," Drug Discovery Today, vol. 10, No. 9, pp. 643-651 (May 1, 2005).
Absynth Biologics Limited, "International Preliminary Report on Patentability and Written Opinion," Int'l Patent Application No. PCT/GB2010/001722, filed Sep. 13, 2010 (Apr. 11, 2012).

* cited by examiner

*Primary Examiner* — Oluwatosin Ogunbiyi
(74) *Attorney, Agent, or Firm* — Janet Sleath; Speckman Law Group PLLC

(57) ABSTRACT

The invention relates to an antigenic polypeptide referred to as DivlB and variants thereof, vaccines comprising said polypeptide and the use of the vaccine in protecting subjects from microbial infection.

19 Claims, 6 Drawing Sheets

Figure 2a

ATGGATGATAAAACGAAGAACGATCAACAAGAATCAAATGAAGATAAAGATGAATTAGAATTATTTACG
AGGAATACATCTAAGAAAAGACGGCAAAGAAAAAGATCAAAGGCTACACATTTTTCTAATCAAAATAAA
GATGATACATCTCAACAAGCTGATTTTGATGAAGAAATTTACTTGATAAATAAAGACTTCAAAAAAGAA
GAAAGCAATGATAAAAATAATGATTCTGCTTCTAGTCATGCGAATGATAATAATATCGATGATTCTACA
GACTCTAATATTGAAAATGAGGATTATAGATATAATCAAGAAATTGACGACCAAAATGAATCGAATGTA
ATTTCAGTCGACAACGAACAACCTCAATCAGCTCCTAAAGAACAAAATAGCGACTCGATTGATGAGGAA
ACAGTAACGAAAAAGAACGAAAAAGTAAAGTAACACAATTAAAGCCATTAACACTTGAAGAAAAGCGG
AAGTTAAGACGTAAGCGACAAAAGCGAATCCAATACAGTGTTATTACAATATTGGTATTGTTGATTGCT
GTTATATTAATTTACATGTTTTCACCACTTAGTAAAATTGCGCATGTAAATATAAATGGAAATAATCAC
GTTAGTACTTCAAAGATAAACAAAGTTTTAGGTGTTAAAAATGATTCAAGGATGTATACGTTTAGTAAA
AAAAATGCTATTAATGATCTCGAAGAGAATCCATTAATCAAAAGTGTTGAGATACACAAGCAATTACCA
AACACATTAAACGTAGATATCACAGAAATGAAATTATTGCTTTAGTGAAATATAAAGGTAAATATTTA
CCTTTATTAGAAAATGGTAAATTGCTTAAAGGTTCAAATGATGTCAAAATTAATGATGCACCTGTCATG
GATGGTTTCAAAGGTACAAAAGAAGATGATATGATTAAGGCGTTATCTGAAATGACACCTGAAGTTAGA
CGATATATTGCCGAAGTGACATACGCCCCAAGTAAAAACAAACAAAGCAGAATTGAATTGTTTACGACA
GATGGACTTCAAGTAATCGGTGATATTTCGACGATATCTAAGAAAATGAAATATTATCCGCAGATGTCA
CAATCATTATCAAGGGATAGTTCGGGTAAACTAAAAACACGAGGCTATATTGATTTATCAGTCGGTGCT
TCATTTATCCCATACCGTGGAAACACGTCTAGTCAATCAGAAAGCGATAAAAATGTGACTAAATCATCT
CAAGAGGAAAATCAAGCAAAAGAAGAATTACAAAGCGTTTTAAACAAAATTAACAAACAATCAAGTAAG
AATAATTAA

Figure 2b

MDDKTKNDQQESNEDKDELELFTRNTSKKRRQRKRSKATHFSNQNKDDTSQQADFDEEIYLINKDFKKE
ESNDKNNDSASSHANDNNIDDSTDSNIENEDYRYNQEIDDQNESNVISVDNEQPQSAPKEQNSDSIDEE
TVTKKERKSKVTQLKPLTLEEKRKLRRKRQKRIQYSVITILVLLIAVILIYMFSPLSKIAHVNINGNNH
VSTSKINKVLGVKNDSRMYTFSKKNAINDLEENPLIKSVEIHKQLPNTLNVDITENEIIALVKYKGKYL
PLLENGKLLKGSNDVKINDAPVMDGFKGTKEDDMIKALSEMTPEVRRYIAEVTYAPSKNKQSRIELFTT
DGLQVIGDISTISKKMKYYPQMSQSLSRDSSGKLKTRGYIDLSVGASFIPYRGNTSSQSESDKNVTKSS
QEENQAKEELQSVLNKINKQSSKNN

Figure 3a

CCACTTAGTAAAATTGCGCATGTAAATATAAATGGAAATAATCACGTTAGTACTTCAAAGATAAACAAA
GTTTTAGGTGTTAAAAATGATTCGAGGATGTATACGTTTAGTAAAAAAAATGCTATTAATGATCTCGAA
GAGGATCCATTAATCAAAAGTGTTGAGATACACAAGCAATTACCAAACACATTAAACGTAGATATCACA
GAAAATGAAATTATTGCTTTAGTGAAATATAAAGGTAAATATTTACCTTTATTAGAAAATGGTAAATTG
CTTAAAGGTTCAAATGATGTCAAAATTAATGATGCACCTGTCATGGATGGTTTCAAAGGTACAAAAGAA
GATGATATGATTAAGGCGTTATCTGAAATGACACCTGAAGTTAGACGATATATTGCCGAAGTGACATAC
GCCCCAAGTAAAAACAAACAAAGCAGAATTGAATTGTTTACGACAGATGGACTTCAAGTAATCGGTGAT
ATTTCGACGATATCTAAGAAAATGAAATATTATCCGCAGATGTCACAATCATTATCAAGGGATAGTTCG
GGTAAACTAAAAACAAGAGGCTATATTGATTTATCAGTCGGTGCTTCATTTATCCCATACCGTGGAAAC
ACGTCTAGTCAATCAGAAAGCGATAAAAATGTGACTAAATCATCTCAAGAGGAAAATCAAGCAAAAGAA
GAATTACAAAGCGTTTTAAACAAAATTAACAAACAATCAAGTAAGAATAAT

Figure 3b

PLSKIAHVNINGNNHVSTSKINKVLGVKNDSRMYTFSKKNAINDLEEDPLIKSVEIHKQLPNTLNVDIT
ENEIIALVKYKGKYLPLLENGKLLKGSNDVKINDAPVMDGFKGTKEDDMIKALSEMTPEVRRYIAEVTY
APSKNKQSRIELFTTDGLQVIGDISTISKKMKYYPQMSQSLSRDSSGKLKTRGYIDLSVGASFIPYRGN
TSSQSESDKNVTKSSQEENQAKEELQSVLNKINKQSSKNN

Figure 4a

ATGGCTCCACTTAGTAAAATTGCGCATGTAAATATAAATGGAAATAATCACGTTAGTACTTCAAAGATA
AACAAAGTTTTAGGTGTTAAAAATGATTCGAGGATGTATACGTTTAGTAAAAAAAATGCTATTAATGAT
CTCGAAGAGGATCCATTAATCAAAAGTGTTGAGATACACAAGCAATTACCAAACACATTAAACGTAGAT
ATCACAGAAAATGAAATTATTGCTTTAGTGAAATATAAAGGTAAATATTTACCTTTATTAGAAAATGGT
AAATTGCTTAAAGGTTCAAATGATGTCAAAATTAATGATGCACCTGTCATGGATGGTTTCAAAGGTACA
AAAGAAGATGATATGATTAAGGCGTTATCTGAAATGACACCTGAAGTTAGACGATATATTGCCGAAGTG
ACATACGCCCCAAGTAAAAACAAACAAAGCAGAATTGAATTGTTTACGACAGATGGACTTCAAGTAATC
GGTGATATTTCGACGATATCTAAGAAAATGAAATATTATCCGCAGATGTCACAATCATTATCAAGGGAT
AGTTCGGGTAAACTAAAAACAAGAGGCTATATTGATTTATCAGTCGGTGCTTCATTTATCCCATACCGT
GGAAACACGTCTAGTCAATCAGAAAGCGATAAAAATGTGACTAAATCATCTCAAGAGGAAAATCAAGCA
AAAGAAGAATTACAAAGCGTTTTAAACAAAATTAACAAACAATCAAGTAAGAATAATCTCGAGCACCAC
CACCACCACCACTGA

Figure 4b

MAPLSKIAHVNINGNNHVSTSKINKVLGVKNDSRMYTFSKKNAINDLEEDPLIKSVEIHKQLPNTLNVD
ITENEIIALVKYKGKYLPLLENGKLLKGSNDVKINDAPVMDGFKGTKEDDMIKALSEMTPEVRRYIAEV
TYAPSKNKQSRIELFTTDGLQVIGDISTISKKMKYYPQMSQSLSRDSSGKLKTRGYIDLSVGASFIPYR
GNTSSQSESDKNVTKSSQEENQAKEELQSVLNKINKQSSKNNLEHHHHHH*

STAPHYLOCOCCUS AUREUS DIV1B FOR USE AS VACCINE

REFERENCE TO RELATED APPLICATIONS

This application is the US national phase entry of International Patent Application No. PCT/GB2010/001722, filed Sep. 13, 2010, which claims priority to GB Patent Application No. 0917685.0, filed Oct. 9, 2009.

FIELD OF THE INVENTION

The invention relates to an antigenic polypeptide, vaccines comprising said polypeptide and the use of the vaccine in protecting subjects from microbial infection.

BACKGROUND

Vaccines protect against a wide variety of infectious diseases. Many vaccines are produced by inactivated or attenuated pathogens which are injected into a subject. The immunised subject responds by producing both a humoral (e.g. antibody) and cellular (e.g. cytolytic T cells) responses. For example, some influenza vaccines are made by inactivating the virus by chemical treatment with formaldehyde. For many pathogens chemical or heat inactivation while it may give rise to vaccine immunogens that confer protective immunity also gives rise to side effects such as fever and injection site reactions. In the case of bacteria, inactivated organisms tend to be so toxic that side effects have limited the application of such crude vaccine immunogens (e.g. the cellular pertussis vaccine) and therefore vaccine development has lagged behind drug-development. Moreover, effective vaccine development using whole cell inactivated organisms suffers from problems of epitope masking, immunodominance, low antigen concentration and antigen redundancy. This is unfortunate as current antibiotic treatments are now prejudiced by the emergence of drug-resistant bacteria.

Many modern vaccines are therefore made from protective antigens of the pathogen, isolated by molecular cloning and purified from the materials that give rise to side-effects. These latter vaccines are known as 'subunit vaccines'. The development of subunit vaccines has been the focus of considerable research in recent years. The emergence of new pathogens and the growth of antibiotic resistance have created a need to develop new vaccines and to identify further candidate molecules useful in the development of subunit vaccines. Likewise the discovery of novel vaccine antigens from genomic and proteomic studies is enabling the development of new subunit vaccine candidates, particularly against bacterial pathogens. However, although subunit vaccines tend to avoid the side effects of killed or attenuated pathogen vaccines, their 'pure' status means that subunit vaccines do not always have adequate immunogenicity to confer protection.

An example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this pathogen can cause infection. This is a particular problem in hospitals where patients may have surgical procedures and/or be taking immunosuppressive drugs. These patients are much more vulnerable to infection with *S. aureus* because of the treatment they have received. Antibiotic resistant strains of *S. aureus* have arisen since their wide spread use in controlling microbial infection. Methicillin resistant strains are prevalent and many of these resistant strains are also resistant to several other antibiotics.

Currently there is no effective vaccination procedure for *S. aureus*.

*S. aureus* is therefore a major human pathogen capable of causing a wide range of diseases some of which are life threatening diseases including septicaemia, endocarditis, arthritis and toxic shock. This ability is determined by the versatility of the organism and its arsenal of components involved in virulence. At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. The pathogen also has the ability to evade host defenses by the production of factors that reduce phagocytosis or interfere with the ability of the cells to be recognised by circulating antibodies. Often a focus of infection develops as an abscess and the number of organisms increases. *S. aureus* has the ability to monitor its own cell density by the production of a quorum sensing peptide. Accumulation of the peptide, associated with physiological changes brought about by the beginning of starvation of the cells, elicits a switch in virulence determinant production from adhesins to components involved in invasion and tissue penetration.

SUMMARY

This disclosure relates to the identification of an antigenic polypeptide, DivIB, isolated and characterized from the gram positive bacterium *S. aureus*. DivIB is an integral membrane protein comprising an intracellular domain [amino acids 1-171] and intermembrane domain [amino acids 172-192] and an extracellular domain [amino acids 193-439]. This is schematically illustrated in FIG. 1. DivIB and fragments thereof, is shown to provide protection from at least an *S. aureus* challenge and represents a novel vaccine candidate. DivIB homolgues are referred to as FtsQ in gram negative bacteria.

According to an aspect of the invention there is provided a polypeptide selected from the group consisting of:
 i) a polypeptide encoded by a nucleotide sequence as represented in FIG. 2a, 3a, or 4a (SEQ ID NO: 1, 3 or 5), or an antigenic fragment thereof;
 a polypeptide encoded by a nucleotide sequence wherein said sequence is degenerate as a result of the genetic code to the nucleotide sequence defined in (i);
 iii) a polypeptide comprising an amino acid sequence wherein said sequence is modified by addition deletion or substitution of at least one amino acid residue as represented in FIG. 2b, 3b or 4b (SEQ ID NO: 2, 4 or 6), wherein said polypeptide is for use as a vaccine.

A modified polypeptide or variant polypeptide may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In one embodiment, the variant polypeptides have at least 85% identity, more preferably at least 90% identity, even more preferably at least 95% identity, still more preferably at least 97% identity, and most preferably at least 99% identity with the full length amino acid sequences illustrated herein.

In a preferred embodiment of the invention said polypeptide is encoded by a nucleotide sequence as represented in FIG. 2a (SEQ ID NO: 1).

In an alternative preferred embodiment of the invention said polypeptide is represented by the amino acid sequence in FIG. 2b (SEQ ID NO: 2), or antigenic part thereof.

In a preferred embodiment of the invention said polypeptide is encoded by a nucleotide sequence as represented in FIG. 3a (SEQ ID NO: 3).

In an alternative preferred embodiment of the invention said polypeptide is represented by the amino acid sequence in FIG. 3b (SEQ ID NO: 4), or antigenic part thereof.

In a preferred embodiment of the invention said polypeptide is encoded by a nucleotide sequence as represented in FIG. 4a (SEQ ID NO: 5).

In an alternative preferred embodiment of the invention said polypeptide is represented by the amino acid sequence in FIG. 4b (SEQ ID NO: 6), or antigenic part thereof.

According to a further aspect of the invention there is provided a vaccine composition for use in the vaccination against a microbial infection, comprising a polypeptide selected from the group consisting of:
  i) a polypeptide encoded by a nucleotide sequence as represented in FIG. 2a, 3a or 4a (SEQ ID NO: 1, 3, or 5), or an antigenic fragment thereof;
  ii) a polypeptide encoded by a nucleotide sequence wherein said sequence is degenerate as a result of the genetic code to the nucleotide sequence defined in (i);
  iii) a polypeptide comprising an amino acid sequence wherein said sequence is modified by addition deletion or substitution of at least one amino acid residue as represented in FIG. 2b, 3b or 4b (SEQ ID NO: 2, 4 or 6):
  wherein said composition optionally includes an adjuvant and/or carrier.

In a preferred embodiment of the invention said composition includes an adjuvant and/or carrier.

In a preferred embodiment of the invention said adjuvant is selected from the group consisting of: cytokines selected from the group consisting of GMCSF, interferon gamma, interferon alpha, interferon beta, interleukin 12, interleukin 23, interleukin 17, interleukin 2, interleukin 1, TGF, TNFα, and TNFβ.

In a further alternative embodiment of the invention said adjuvant is a TLR agonist such as CpG oligonucleotides, flagellin, monophosphoryl lipid A, poly I:C and derivatives thereof.

In a preferred embodiment of the invention said adjuvant is a bacterial cell wall derivative such as muramyl dipeptide (MDP) and/or trehalose dicorynomycolate (TDM).

An adjuvant is a substance or procedure which augments specific immune responses to antigens by modulating the activity of immune cells. Examples of adjuvants include, by example only, agonistic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter. The term carrier is construed in the following manner. A carrier is an immunogenic molecule which, when bound to a second molecule augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen.

In a preferred embodiment of the invention said microbial infection is caused by a bacterial species selected from the group consisting of: *Staphylococcus* spp, *Enterococcus faecalis, Mycobacterium tuberculosis, Streptococcus* group B, *Streptococcus pneumoniae, Helicobacter pylori, Neisseria gonorrhoea, Streptococcus* group A, *Borrelia burgdorferi, Coccidiodes immitis, Histoplasma capsulatum, Klebsiella edwardii, Neisseria meningitidis* type B, *Proteus mirabilis, Shigella flexneri, Escherichia coli, Haemophilus influenzae, Chlamydia trachomatis, Chlamydia pneumoniae, Chlamydia psittaci, Francisella tularensis, Pseudomonas aeruginosa, Bacillus anthracis, Clostridium botulinum, Yersinia pestis, Burkholderia mallei* or *B. pseudomallei*.

In a preferred embodiment of the invention said bacterial species is selected from the group consisting of: *S. epidermidis, S. aureus, S. hominis, S. haemolyticus, S. wameri, S. capitis, S. saccharolyticus, S. auricularis, S. simulans, S. saprophyticus, S. xylosus, S. hyicus, S. caprae, S. gallinarum, S. intermedius.*

In a further preferred embodiment of the invention said staphylococcal cell is *S. aureus* or *S. epidermidis*.

The vaccine compositions of the invention can be administered by any conventional route, including injection, intranasal spray by inhalation of for example an aerosol or nasal drops. The administration may be, for example, intravenous, intraperitoneal, intramuscular, intracavity, subcutaneous, or intradermally I. The vaccine compositions of the invention are administered in effective amounts. An "effective amount" is that amount of a vaccine composition that alone or together with further doses, produces the desired response. In the case of treating a particular bacterial disease the desired response is providing protection when challenged by an infective agent.

In a preferred embodiment of the invention said vaccine composition is adapted for administration as a nasal spray.

In a preferred embodiment of the invention said vaccine composition is provided in an inhaler and delivered as an aerosol.

The amounts of vaccine will depend, of course, on the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used sufficient to provoke immunity; that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of vaccine administered to a subject can be chosen in accordance with different parameters, in particular in accordance with the mode of administration used and the state of the subject. In the event that a response in a subject is insufficient at the initial doses applied, higher doses (or effectively higher doses by a different, more localized delivery route) may be employed to the extent that patient tolerance permits.

In general, doses of vaccine are formulated and administered in effective immunizing doses according to any standard procedure in the art. Other protocols for the administration of the vaccine compositions will be known to one of ordinary skill in the art, in which the dose amount, schedule of injections, sites of injections, mode of administration and the like vary from the foregoing. Administration of the vaccine compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep or goat.

In a preferred embodiment of the invention there is provided a vaccine composition according to the invention that includes at least one additional anti-bacterial agent.

In a preferred embodiment of the invention said agent is a second different vaccine and/or immunogenic agent (for example a bacterial polypeptide and/or polysaccharide antigen).

According to a further aspect of the invention there is provided a polypeptide as herein described for use in the treatment of microbial infections or conditions that result from microbial infections.

In a preferred embodiment of the invention said microbial infection is a staphyloccal infection.

In a preferred embodiment of the invention said condition that results from a microbial infection is selected from the group consisting of: tuberculosis, bacteria-associated food poisoning, blood infections, peritonitis, endocarditis, osteomyelitis, sepsis, skin disorders, meningitis, pneumonia, stomach ulcers, gonorrhoea, strep throat, streptococcal-associated toxic shock, necrotizing fasciitis, impetigo, histoplasmosis, Lyme disease, gastro-enteritis, dysentery, shigellosis, and arthritis.

According to a further aspect of the invention there is provided a method to immunize a subject comprising vaccinating said subject with an effective amount of the polypeptide, nucleic acid molecule or vaccine composition according to the invention.

In a preferred method of the invention said subject is a human.

In an alternative preferred method of the invention said subject is an animal, preferably a livestock animal, for example cattle.

In a preferred method of the invention said live stock animal is vaccinated against bacterial mastitis caused by staphylococcal bacterial cells.

In a preferred method of the invention said life stock animal is a caprine animal (e.g. sheep, goat).

In a preferred method of the invention said life stock animal is a bovine animal (e.g. a cow).

Staphylococcal mastitis is a serious condition that affects live stock and can result in considerable expense with respect to controlling the disease through administration of antibiotics and in terms of lost milk yield. The vaccine according to the invention provides cost effective control of bacterial, in particular staphylococcal mastitis.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures:

FIG. 2a illustrates the full DivIB nucleotide sequence from S. aureus8325(SEQ ID NO: 1);

FIG. 2b illustrates the amino acid sequence from S. aureus8325(SEQ ID NO: 2) and corresponds to the GeneBank ID number ABD30258.1;

FIG. 3a illustrates the nucleotide sequence (SEQ ID NO: 3) and FIG. 3b the amino acid sequence (SEQ ID NO: 4) of the extramembranous fragment of the S. aureus DivIB (DiviB-1) that encompasses amino acids 193 through 439;

FIG. 4a illustrates the nucleotide sequence (SEQ ID NO: 5) and FIG. 4b the amino acid sequence (SEQ ID NO: 6) of DivIB-2.

DETAILED DESCRIPTION

Figure 1:
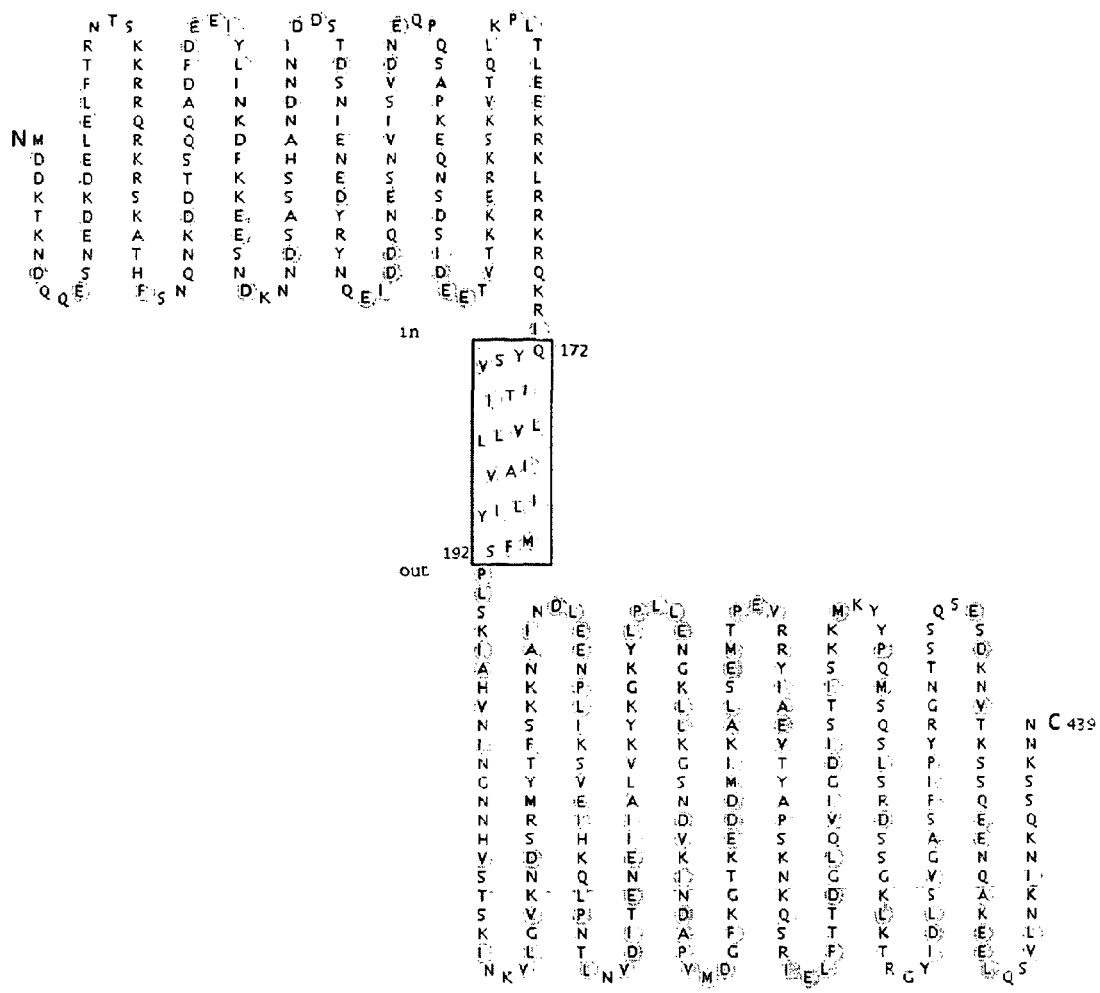
FIG. 1 The DivIB protein is predicted to be a membrane proteins with the majority model topological distribution indicated. The N-terminal of the protein (aminoacids 1 through 171) is located inside of the cell, while the C-terminal of the protein (aminoacids 193 through 439) is exposed on the outside of the membrane; the predicted external portion of the S. aureus DivIB (aminoacids 193 through 439) corresponds to the fragment termed DivIB-1.

Materials and Methods
Construction of plasmid for the overexpression of the DivIB-1 Fragment from S. aureus in E. coli Fragment DivIB-1 was PCR amplified from the chromosome of strain S. aureus SH1000 (Horsburgh M J, Aish J L, White I J, Shaw L, Lithgow J K, Foster S J: sigmaB modulates virulence determinant expression and stress resistance: characterization of a functional rsbU strain derived from Staphylococcus aureus 8325-4. J Bacteriol 2002, 184:5457-5467) using primers 5'GLUSh341C and 3' GLUSh341C (corresponding to sequences primer 1 and primer 2 respectively) and the following PCR reaction conditions: 1 initial denaturation cycle of 94° C. for 4 min; 30 amplification cycles of denaturation 94° C. for 30 seconds, annealing 45° C. for 30 seconds, and extension at 72° C. for 2.5 seconds; finally, ongoing amplification rounds were allow to complete at 72° C. for 4 min. Two restrictions sites were engineered within primers 5'GLUSh341C and 3' GLUSh341C, NcoI and XhoI, respectively (underlined in the sequence). Fragment DivIB-1 digested with NcoI and XhoI was cloned into the NcoI and XhoI sites from pET-21d (+) from Novagen (Cat. No. 69743-3) resulting in the overexpression plasmid named pGL601 generating a 6×His-tagged form of the DivIB-1 fragment. The latter was transferred into E. coli BL21 for overexpresion of the recombinant protein fragment.

```
Primer 1 (5'GLUSh341C)
ATAATACCATGGCTCCACTTAGTAAAATTGCGCATG    SEQ ID NO: 7

Primer 2 (3'GLUSh341C)
ATAATACTCGAGATTATTCTTACTTGATTGTTTG      SEQ ID NO: 8
```

The cloning of the PCR amplified fragment indicated above into the recipient pET21d(+) recipient plasmid vector at the NcoI and XhoI sites entailed the addition of two aminoacids (methionine and alanine) upstream of the DivlB-1 sequence and eight aminoacids (leucine, glutamate and six histidines) downstream of the DivlB-1 sequence. This whole region encompasses the protein fragment to be produced from the ATG translational start codon to the TGA translational stop codon (indicated in bold within the sequence), and named DivlB-2. The DNA (FIG. 4a) and protein (FIG. 4b) sequences of DivlB-2 are indicated below and the supplementary nucleotides to the DivlB-1 fragment are underlined.

EXAMPLE

Vaccinations with DivlB-2 Protect Balb/C Mice Against *S. aureus* Infections

In each experiment, a group of 10 female Balb/C 6 to 12 weeks old were vaccinated with DivlB-2 according to the following protocol. Each animal was primed with 100 microliters of a solution made up of a mixture 50 micrograms of recombinant DivlB-2 (approximately 98% purity) in 50 microliters endotoxin-free PBS (Phosphate Buffer Saline pH 7.4) and 50 microliters of Complete Freund's adjuvant. Two weeks later the animals were boosted with 100 microliters of a solution made up of a mixture 50 micrograms of recombinant DivlB-2 (approximately 98% purity) in 50 microliters of endotoxin-free PBS and 50 microliters of Incomplete Freund's adjuvant. A week later the animals received an identical boost. In each experiment, a control group of 10 animals were treated following an identical protocol except for the fact that instead of the DivlB-2 recombinat protein the mixture contained commercially available KLH protein (Keyhole limpet hemocyanin).

Priming and boost injections were performed intradermally in the back of the neck of the animals.

One week after the second boost each animal was infected with an i.v. (tail vein) injection of 100 microliters of endotoxin-free PBS containing $1.1 \times 10^7$ ($\pm 0.3 \times 10^7$) cells of *S. aureus* strain Newman. The latter were prepared from cultures growing to early stationary phase in Brain Heart Infusion medium (BHI), which was then washed three times with the same volume of PBS.

After 10 to 14 days the animals were sacrificed according to Schedule 1 cervical dislocation. The pair of kidneys from each animal was extracted in aseptic conditions, and homogenized in sterile PBS. Serial dilutions of the kidney homogenates were carried out in PBS and plated on BHI agar plates. Plates containing between 10 to 150 staphylococcal colonies were counted and dilution corrected. The number of viable cells in the kidneys was inferred from the number of colony forming units (CFU) on the plates. Evaluation of the possible protection against infection conferred by vaccination with DivlB-2 was determined from difference in the number of *S. aureus* cells in the kidneys of animals vaccinated with KLH and those vaccinated with DivlB-2. The statistic significance of the difference was calculated using the Mann-Whitney test. A significantly higher ($p<0.05$) number of *S. aureus* in KLH vaccinated animals compared to the DivlB-2 vaccinated animals was concluded as protection.

Figure 5:
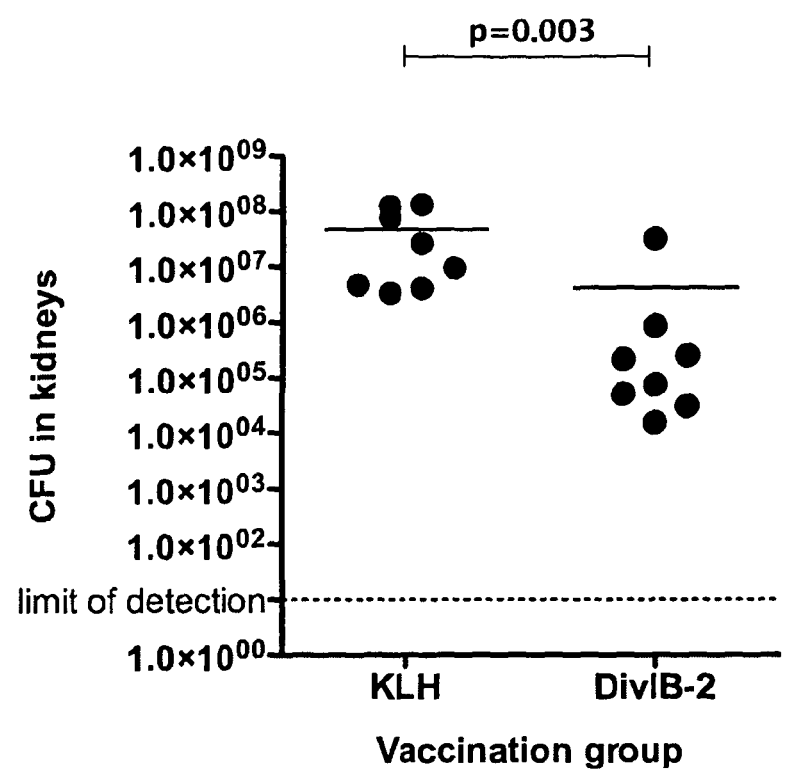
FIG. 5 and FIG. 6 illustrate the protection against infection conferred by DivIB-2 vaccination.
Figure 6:
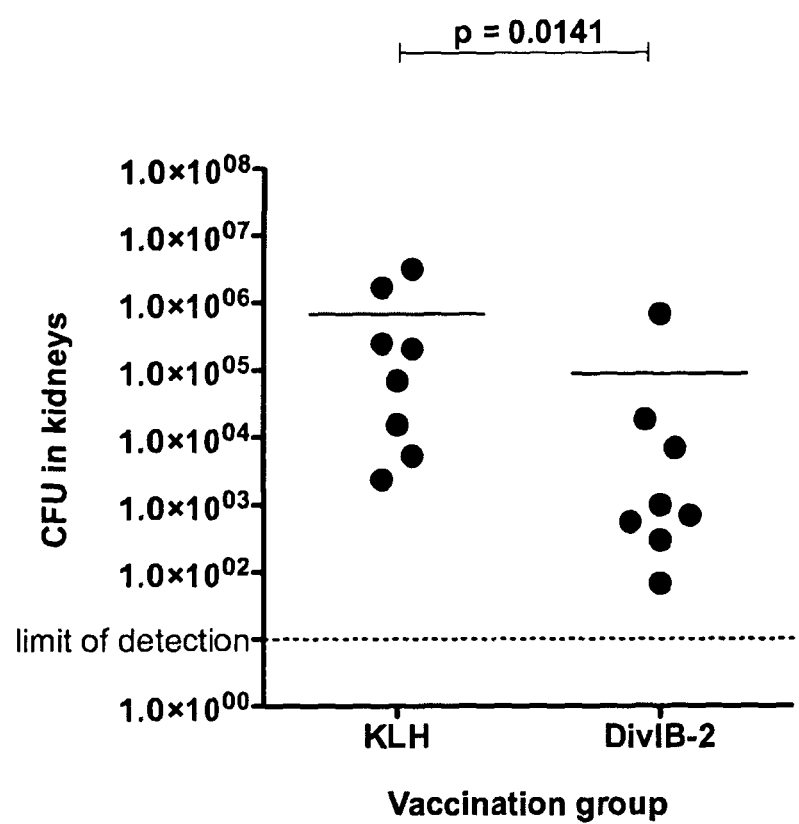

Examples of the experiments described above and illustrating the protection against infection conferred by DivlB-2 vaccination are shown in FIG. 5 and FIG. 6. The mean for each group and the statistically significant difference between the control and the vaccinated group are indicated.

The invention claimed is:

1. An isolated polypeptide selected from the group consisting of:
   i) a polypeptide encoded by the nucleotide sequence of SEQ ID NO: 3 or 5;
   ii) a polypeptide encoded by a nucleotide sequence wherein said sequence is degenerate as a result of the genetic code to the nucleotide sequence defined in (i); and
   iii) the polypeptide consisting of SEQ ID NO: 4 or 6, wherein said polypeptide is antigenic.

2. The isolated polypeptide according to claim 1 wherein said polypeptide is encoded by of SEQ ID NO: 3.

3. The isolated polypeptide according to claim 1 wherein said polypeptide consists of SEQ ID NO: 4.

4. The isolated polypeptide according to claim 1 wherein said polypeptide is encoded by SEQ ID NO: 5.

5. The isolated polypeptide according to claim 1 wherein said polypeptide consists of SEQ ID NO: 6.

6. An immunogenic composition for use in immunizing against a Staphylococcal infection, comprising a polypeptide selected from the group consisting of:
   i) a polypeptide encoded by the nucleotide sequence of SEQ ID NO: 3 or 5;
   ii) a polypeptide encoded by a nucleotide sequence wherein said sequence is degenerate as a result of the genetic code to the nucleotide sequence defined in (i); and
   iii) the polypeptide consisting of SEQ ID NO: 4 or 6;
   wherein said immunogenic composition includes an adjuvant and/or carrier.

7. The immunogenic composition according to claim 6 wherein said Staphylococcal infection is caused by a bacterial species selected from the group consisting of: *S. epidermidis, S. aureus, S. hominis, S. haemolyticus, S. warneri, S. capitis, S. saccharolyticus, S. auricularis, S. simulans, S. saprophyticus, S. cohnii, S. xylosus, S. hyicus, S. caprae, S. gallinarum, and S. intermedius.*

8. The immunogenic composition according to claim 7 wherein said bacterial species is *S. aureus* or *S. epidermidis.*

9. The immunogenic composition according to claim 6 wherein said immunogenic composition is adapted for administration as a nasal spray.

10. The immunogenic composition according to claim 6 wherein said immunogenic composition includes at least one additional anti-bacterial agent.

11. The immunogenic composition according to claim 10 wherein said agent is a second different vaccine and/or immunogenic agent.

12. A method for the treatment of Staphylococcal infections or conditions that result from Staphylococcal infections in a subject, comprising administering to the subject a polypeptide of claim 1.

13. The method of claim 12 wherein said condition that results from a Staphylococcal infection is selected from the group consisting of: Staphylococcal associated food poisoning, blood infections, peritonitis, endocarditis, osteomyelitis, sepsis, skin disorders, meningitis, pneumonia, necrotizing fasciitis, impetigo, gastro-enteritis, dysentery, toxic shock, and arthritis.

14. A method to immunize a subject against a Staphylococcal infection or a condition that results from a Staphylococcal infection comprising administering to said subject an effective amount of the polypeptide of claim 1.

15. The method according to claim 14 wherein said subject is a human.

16. The method according to claim 14 wherein said subject is a livestock animal.

17. The method according to claim 16 wherein said condition is bacterial mastitis caused by staphylococcal bacterial cells.

18. The method according to claim 17 wherein said livestock animal is a caprine animal or a bovine animal.

19. A method to immunize a subject against a Staphylococcal infection or a condition that results from a Staphylococcal infection, comprising administering to said subject an effective amount of the immunogenic composition of claim 6.

* * * * *

SEQUENCE LISTING

```
<160> NUMBER OF SEQ ID NOS: 8

<210> SEQ ID NO 1
<211> LENGTH: 1320
<212> TYPE: DNA
<213> ORGANISM: Staphylococcus aureus

<400> SEQUENCE: 1
atggatgata aaacgaagaa cgatcaacaa gaatcaaatg aagataaaga tgaattagaa      60
ttatttacga ggaatacatc taagaaaaga cggcaaagaa aaagatcaaa ggctacacat     120
ttttctaatc aaaataaaga tgatacatct caacaagctg attttgatga agaaatttac     180
ttgataaata aagacttcaa aaaagaagaa agcaatgata aaaataatga ttctgcttct     240
agtcatgcga atgataataa tatcgatgat tctacagact ctaatattga aaatgaggat     300
tatagatata atcaagaaat tgacgaccaa aatgaatcga atgtaatttc agtcgacaac     360
gaacaacctc aatcagctcc taagaacaa aatagcgact cgattgatga ggaaacagta     420
acgaaaaaag aacgaaaaag taaagtaaca caattaaagc cattaacact tgaagaaag      480 cggaagttaa gacgtaagcg acaaaagcga atccaataca gtgttattac aatattggta     540
ttgttgattg ctgttatatt aatttacatg ttttcaccac ttagtaaaat tgcgcatgta     600
aatataaatg gaaataatca cgttagtact tcaaagataa acaagttttt aggtgttaaa     660
aatgattcaa ggatgtatac gtttagtaaa aaaaatgcta ttaatgatct cgaagagaat     720
```

```
ccattaatca aaagtgttga gatacacaag caattaccaa acacattaaa cgtagatatc    780
acagaaaatg aaattattgc tttagtgaaa tataaaggta aatatttacc tttattagaa    840
aatggtaaat tgcttaaagg ttcaaatgat gtcaaaatta atgatgcacc tgtcatggat    900
ggtttcaaag gtacaaaaga agatgatatg attaaggcgt tatctgaaat gacacctgaa    960
gttagacgat atattgccga agtgacatac gccccaagta aaacaaaca aagcagaatt   1020 gaattgttta cgacagatgg acttcaagta atcggtgata tttcgacgat atctaagaaa   1080
atgaaatatt atccgcagat gtcacaatca ttatcaaggg atagttcggg taaactaaaa   1140
acacgaggct atattgattt atcagtcggt gcttcattta tcccataccg tggaaacacg   1200
tctagtcaat cagaaagcga taaaaatgtg actaaatcat ctcaagagga aaatcaagca   1260
aaagaagaat tacaaagcgt tttaaacaaa attaacaaac aatcaagtaa gaataattaa   1320
```

<210> SEQ ID NO 2
<211> LENGTH: 439
<212> TYPE: PRT
<213> ORGANISM: Staphylococcus aureus

<400> SEQUENCE: 2

```
Met Asp Asp Lys Thr Lys Asn Asp Gln Gln Glu Ser Asn Glu Asp Lys
1               5                   10                  15

Asp Glu Leu Glu Leu Phe Thr Arg Asn Thr Ser Lys Lys Arg Arg Gln
            20                  25                  30

Arg Lys Arg Ser Lys Ala Thr His Phe Ser Asn Gln Asn Lys Asp Asp
        35                  40                  45

Thr Ser Gln Gln Ala Asp Phe Asp Glu Glu Ile Tyr Leu Ile Asn Lys
    50                  55                  60

Asp Phe Lys Lys Glu Glu Ser Asn Asp Lys Asn Asn Asp Ser Ala Ser
65                  70                  75                  80

Ser His Ala Asn Asp Asn Asn Ile Asp Asp Ser Thr Asp Ser Asn Ile
                85                  90                  95

Glu Asn Glu Asp Tyr Arg Tyr Asn Gln Glu Ile Asp Asp Gln Asn Glu
            100                 105                 110

Ser Asn Val Ile Ser Val Asp Asn Glu Gln Pro Gln Ser Ala Pro Lys
        115                 120                 125

Glu Gln Asn Ser Asp Ser Ile Asp Glu Glu Thr Val Thr Lys Lys Glu
    130                 135                 140

Arg Lys Ser Lys Val Thr Gln Leu Lys Pro Leu Thr Leu Glu Glu Lys
145                 150                 155                 160

Arg Lys Leu Arg Arg Lys Arg Gln Lys Arg Ile Gln Tyr Ser Val Ile
                165                 170                 175

Thr Ile Leu Val Leu Leu Ile Ala Val Ile Leu Ile Tyr Met Phe Ser
            180                 185                 190

Pro Leu Ser Lys Ile Ala His Val Asn Ile Asn Gly Asn Asn His Val
        195                 200                 205

Ser Thr Ser Lys Ile Asn Lys Val Leu Gly Val Lys Asn Asp Ser Arg
    210                 215                 220

Met Tyr Thr Phe Ser Lys Lys Asn Ala Ile Asn Asp Leu Glu Glu Asn
225                 230                 235                 240

Pro Leu Ile Lys Ser Val Glu Ile His Lys Gln Leu Pro Asn Thr Leu
                245                 250                 255

Asn Val Asp Ile Thr Glu Asn Gly Ile Ile Ala Leu Val Lys Tyr Lys
            260                 265                 270
```

-continued

Gly Lys Tyr Leu Pro Leu Leu Glu Asn Gly Lys Leu Leu Lys Gly Ser
        275                 280                 285

Asn Asp Val Lys Ile Asn Asp Ala Pro Val Met Asp Gly Phe Lys Gly
        290                 295                 300

Thr Lys Glu Asp Asp Met Ile Lys Ala Leu Ser Glu Met Thr Pro Glu
305                 310                 315                 320

Val Arg Arg Tyr Ile Ala Glu Val Thr Tyr Ala Pro Ser Lys Asn Lys
                325                 330                 335

Gln Ser Arg Ile Glu Leu Phe Thr Thr Asp Gly Leu Gln Val Ile Gly
            340                 345                 350

Asp Ile Ser Thr Ile Ser Lys Lys Met Lys Tyr Pro Gln Met Ser
        355                 360                 365

Gln Ser Leu Ser Arg Asp Ser Ser Gly Lys Leu Lys Thr Arg Gly Tyr
    370                 375                 380

Ile Asp Leu Ser Val Gly Ala Ser Phe Ile Pro Tyr Arg Gly Asn Thr
385                 390                 395                 400

Ser Ser Gln Ser Glu Ser Asp Lys Asn Val Thr Lys Ser Ser Gln Glu
                405                 410                 415

Glu Asn Gln Ala Lys Glu Glu Leu Gln Ser Val Leu Asn Lys Ile Asn
            420                 425                 430

Lys Gln Ser Ser Lys Asn Asn
        435

<210> SEQ ID NO 3
<211> LENGTH: 741
<212> TYPE: DNA
<213> ORGANISM: Staphylococcus aureus

<400> SEQUENCE: 3
ccacttagta aaattgcgca tgtaaatata atggaaata atcacgttag tacttcaaag      60
ataaacaaag ttttaggtgt taaaaatgat tcgaggatgt atacgtttag taaaaaaaat    120
gctattaatg atctcgaaga ggatccatta atcaaagtg ttgagataca aagcaatta     180
ccaaacacat taaacgtaga tatcacagaa atgaaatta ttgctttagt gaaatataaa    240
ggtaaatatt tacctttatt agaaaatggt aaattgctta aaggttcaaa tgatgtcaaa    300
attaatgatg caccctgtcat ggatggtttc aaaggtacaa agaagatga tatgattaag    360
gcgttatctg aaatgacacc tgaagttaga cgatatattg ccgaagtgac atacgcccca    420
agtaaaaaca acaaagcag aattgaattg tttacgacag atggacttca agtaatcggt    480
gatatttcga cgatatctaa gaaatgaaa tattatccgc agatgtcaca atcattatca    540
agggatagtt cgggtaaact aaaaacaaga ggctatattg atttatcagt cggtgcttca    600
tttatcccat accgtggaaa cacgtctagt caatcagaaa gcgataaaaa tgtgactaaa    660
tcatctcaag aggaaaatca agcaaaagaa gaattacaaa gcgttttaaa caaaattaac    720
aaacaatcaa gtaagaataa t                                            741

<210> SEQ ID NO 4
<211> LENGTH: 247
<212> TYPE: PRT
<213> ORGANISM: Staphylococcus aureus

<400> SEQUENCE: 4

Pro Leu Ser Lys Ile Ala His Val Asn Ile Asn Gly Asn Asn His Val
1               5                   10                  15

Ser Thr Ser Lys Ile Asn Lys Val Leu Gly Val Lys Asn Asp Ser Arg
            20                  25                  30

Met Tyr Thr Phe Ser Lys Lys Asn Ala Ile Asn Asp Leu Glu Glu Asp
            35                  40                  45

Pro Leu Ile Lys Ser Val Glu Ile His Lys Gln Leu Pro Asn Thr Leu
 50                  55                  60

Asn Val Asp Ile Thr Glu Asn Glu Ile Ile Ala Leu Val Lys Tyr Lys
 65                  70                  75                  80

Gly Lys Tyr Leu Pro Leu Leu Gly Asn Gly Lys Leu Leu Lys Gly Ser
                 85                  90                  95

Asn Asp Val Lys Ile Asn Asp Ala Pro Val Met Asp Gly Phe Lys Gly
                100                 105                 110

Thr Lys Glu Asp Asp Met Ile Lys Ala Leu Ser Glu Met Thr Pro Glu
            115                 120                 125

Val Arg Arg Tyr Ile Ala Glu Val Thr Tyr Ala Pro Ser Lys Asn Lys
130                 135                 140

Gln Ser Arg Ile Glu Leu Phe Thr Thr Asp Gly Leu Gln Val Ile Gly
145                 150                 155                 160

Asp Ile Ser Thr Ile Ser Lys Lys Met Lys Tyr Tyr Pro Gln Met Ser
                165                 170                 175

Gln Ser Leu Ser Arg Asp Ser Ser Gly Lys Leu Lys Thr Arg Gly Tyr
                180                 185                 190

Ile Asp Leu Ser Val Gly Ala Ser Phe Ile Pro Tyr Arg Gly Asn Thr
            195                 200                 205

Ser Ser Gln Ser Glu Ser Asp Lys Asn Val Thr Lys Ser Ser Gln Glu
210                 215                 220

Glu Asn Gln Ala Lys Glu Glu Leu Gln Ser Val Leu Asn Lys Ile Asn
225                 230                 235                 240

Lys Gln Ser Ser Lys Asn Asn
                245

<210> SEQ ID NO 5
<211> LENGTH: 774
<212> TYPE: DNA
<213> ORGANISM: Staphylococcus aureus

<400> SEQUENCE: 5
atggctccac ttagtaaaat tgcgcatgta aatataaatg gaaataatca cgttagtact      60
tcaaagataa acaaagtttt aggtgttaaa atgattcga ggatgtatac gtttagtaaa     120
aaaaatgcta ttaatgatct cgaagaggat ccattaatca aaagtgttga gatacacaag     180
caattaccaa acacattaaa cgtagatatc acagaaaatg aaattattgc tttagtgaaa     240
tataaaggta atatttacc tttattagaa atggtaaat tgcttaaagg ttcaaatgat      300
gtcaaaatta tgatgcacc tgtcatggat ggtttcaaag gtacaaaaga agatgatatg     360
attaaggcgt tatctgaaat gacacctgaa gttagacgat atattgccga agtgacatac     420
gccccaagta aaacaaaca agcagaatt gaattgttta cgacagatgg acttcaagta      480
atcggtgata tttcgacgat atctaagaaa atgaaatatt atccgcagat gtcacaatca     540
ttatcaaggg atagttcggg taaactaaaa acaagaggct atattgattt atcagtcggt     600
gcttcattta tcccataccg tggaaacacg tctagtcaat cagaaagcga taaaaatgtg     660 actaatcat ctcaagagga aaatcaagca aagaagaat tacaaagcgt tttaaacaaa      720
attaacaaac aatcaagtaa gaataatctc gagcaccacc accaccacca ctga           774

<210> SEQ ID NO 6
<211> LENGTH: 257

```
<212> TYPE: PRT
<213> ORGANISM: Staphylococcus aureus

<400> SEQUENCE: 6

Met Ala Pro Leu Ser Lys Ile Ala His Val Asn Ile Asn Gly Asn Asn
1               5                   10                  15

His Val Ser Thr Ser Lys Ile Asn Lys Val Leu Gly Val Lys Asn Asp
            20                  25                  30

Ser Arg Met Tyr Thr Phe Ser Lys Lys Asn Ala Ile Asn Asp Leu Glu
        35                  40                  45

Glu Asp Pro Leu Ile Lys Ser Val Glu Ile His Lys Gln Leu Pro Asn
    50                  55                  60

Thr Leu Asn Val Asp Ile Thr Glu Asn Glu Ile Ile Ala Leu Val Lys
65                  70                  75                  80

Tyr Lys Gly Lys Tyr Leu Pro Leu Leu Glu Asn Gly Lys Leu Leu Lys
                85                  90                  95

Gly Ser Asn Asp Val Lys Ile Asn Asp Ala Pro Val Met Asp Gly Phe
            100                 105                 110

Lys Gly Thr Lys Glu Asp Asp Met Ile Lys Ala Leu Ser Glu Met Thr
        115                 120                 125

Pro Glu Val Arg Arg Tyr Ile Ala Glu Val Thr Tyr Ala Pro Ser Lys
    130                 135                 140

Asn Lys Gln Ser Arg Ile Glu Leu Phe Thr Thr Asp Gly Leu Gln Val
145                 150                 155                 160

Ile Gly Asp Ile Ser Thr Ile Ser Lys Lys Met Lys Tyr Tyr Pro Gln
                165                 170                 175

Met Ser Gln Ser Leu Ser Arg Asp Ser Ser Gly Lys Leu Lys Thr Arg
            180                 185                 190

Gly Tyr Ile Asp Leu Ser Val Gly Ala Ser Phe Ile Pro Tyr Arg Gly
        195                 200                 205

Asn Thr Ser Ser Gln Ser Glu Ser Asp Lys Asn Val Thr Lys Ser Ser
    210                 215                 220

Gln Glu Glu Asn Gln Ala Lys Glu Glu Leu Gln Ser Val Leu Asn Lys
225                 230                 235                 240

Ile Asn Lys Gln Ser Ser Lys Asn Asn Leu Glu His His His His
                245                 250                 255

His

<210> SEQ ID NO 7
<211> LENGTH: 36
<212> TYPE: DNA
<213> ORGANISM: artificial
<220> FEATURE:
<223> OTHER INFORMATION: forward primer for amplification of DivIB

<400> SEQUENCE: 7
ataataccat ggctccactt agtaaaattg cgcatg                         36

<210> SEQ ID NO 8
<211> LENGTH: 34
<212> TYPE: DNA
<213> ORGANISM: artificial
<220> FEATURE:
<223> OTHER INFORMATION: reverse primer for amplification of DivIB

<400> SEQUENCE: 8
ataatactcg agattattct tacttgattg tttg                           34
```